(12) United States Patent
Goodman et al.

(10) Patent No.: US 6,525,182 B1
(45) Date of Patent: Feb. 25, 2003

(54) GUANIDINYLATION, GUANIDINOGLYCOSIDES, USES, AND METHODS OF ASSAYING THEIR ACTIVITY

(75) Inventors: Murray Goodman, La Jolla, CA (US); Yitzhak Tor, San Diego, CA (US); Tracy Baker, La Jolla, CA (US); Nathan Luedtke, La Jolla, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 09/768,026

(22) Filed: Jan. 22, 2001

Related U.S. Application Data
(60) Provisional application No. 60/177,495, filed on Jan. 21, 2000.

(51) Int. Cl.[7] .............................................. C07H 15/22
(52) U.S. Cl. ..................... 536/13.2; 536/13.3; 536/13.7; 536/14; 536/15; 536/18.5; 514/32; 514/37; 514/41; 514/459; 514/460
(58) Field of Search ................................. 514/459, 460, 514/32, 37, 41; 536/13.2, 13.3, 13.7, 14, 15, 18.5

(56) References Cited

U.S. PATENT DOCUMENTS
6,072,075 A * 6/2000 Goodman et al. .......... 560/158

FOREIGN PATENT DOCUMENTS
WO  WO 95/29926 A1 * 11/1995

OTHER PUBLICATIONS
Abstract to Luts, et al., "2–Deoxystreptamine derivatives", J. Pharm. Sci. 50, pp. 328–330, 1961.*

Abstract to Odo et al., "Guanidination of D–glucosamine", J. Org. Chem. 23, pp. 1319–1321, 1958.*

* cited by examiner

*Primary Examiner*—Dwayne C. Jones
(74) *Attorney, Agent, or Firm*—Gray Cary Ware & Freidenrich, LLP; Lisa A. Haile; June M. Learn

(57) ABSTRACT

Provided are reagents and methods useful for the synthesis of guanidinylated compounds. Also provided are methods for assaying molecules, including guanidinylated molecules that modulate viral infection and replication.

34 Claims, 6 Drawing Sheets

GUANIDINYLATION, GUANIDINOGLYCOSIDES, USES, AND METHODS OF ASSAYING THEIR ACTIVITY

CROSS REFERENCE TO RELATED APPLICATIONS

This application claims priority under 35 U.S.C. §119(e)(1) from Provisional Application Serial No. 60/177,495, filed Jan. 21, 2000, which is incorporated herein by reference in its entirety.

GOVERNMENTAL SUPPORT

The U.S. Government has certain rights in this invention pursuant to Grant No. GM08326 awarded by the National Institute of Health.

BACKGROUND

Many natural compounds that bear a guanidine functional group have biological activity that make them useful as pharmaceuticals. Among these compounds are antimicrobials, antifungals, antivirals, neurotoxins, hormones, and agents that act as agonists or antagonists to biological signals. A review of these natural products is presented in Progress in the Chemistry of Organic Natural Products (1995) 66:119 and Berlinck, R. G. S. (1996) Nat. Prod. Reports 13(5):377–409. Much effort has been directed to developing routes for preparing these compounds or their analogues synthetically.

Guanidine-containing bioactive molecules, particularly the analogs or derivatives of the natural products, are now significant targets for drug design and discovery. The guanidine moiety in the bioactive compound frequently occurs in arginine-containing polypeptide chains which may comprise the entire biomolecule or exist as an incorporated moiety. Arginine, together with lysine, another amino acid with a positively charged side chain, plays an important role in biologically active proteins and peptides. Various arginine analogues and derivatives have been synthesized and incorporated into peptides and peptidomimetics to study the structure-activity relationships of arginine-containing molecules. These residues are frequently the critical amino acid residues in peptidomimetics.

Guanidine-containing sugars and sugar-like molecules have a wide range of biologically important uses such as inhibition of inappropriate mitogenic signaling, therapy for bacterial infections, treatment of non-insulin-dependent diabetes, and inhibition of enzymes including thrombin, glycosidases, and nitric oxide synthases.

The development of novel guanidinylated compounds are useful in methods of treating or modulating disease states and other disorders.

SUMMARY OF THE INVENTION

The present invention provides a guanidinoglycoside produced by reacting a compound having the general formula N,N'-diprotected-N''-triflylguanidine (I) with an aminoglycoside under conditions such that the aminoglycoside is guanidinylated thereby producing the guanidinoglycoside.

In one embodiment, the present invention provides a guanidinoglycoside, including, for example, guanidinylated-Boc protected glycosides.

In another embodiment, the present invention provides a guanidinylated tobramycin.

In another embodiment, the invention provides a guanidinylated glucosamine.

In a yet another embodiment, the present invention provides a guanidinylated 2-deoxystreptamine.

The invention further provides a guanidinylated kanamycin A or kanamycin B and guanidinylated paromomycin.

In yet a further embodiment, the present invention provides a guanidinylated neomycin.

The present invention provides a method for identifying a compound that binds to a HIV-1 Rev protein RNA recognition element (RRE). The method includes incubating components comprising a test compound, the RRE, and a labeled Rev protein under conditions sufficient to allow the components to interact; and detecting the labeled Rev protein, wherein the location or emission of the labeled Rev is indicative of a test compound that binds to the RRE.

The present invention also provides a method of treating a subject having or at risk of having a bacterial or viral infection, comprising, contacting the subject with a guanidinoglycoside in an amount sufficient to inhibit or prevent the bacterial or viral infection. The subject may be any animal, including mammals; preferably the mammal is a human.

DETAILED DESCRIPTION OF THE INVENTION

Figure 1:
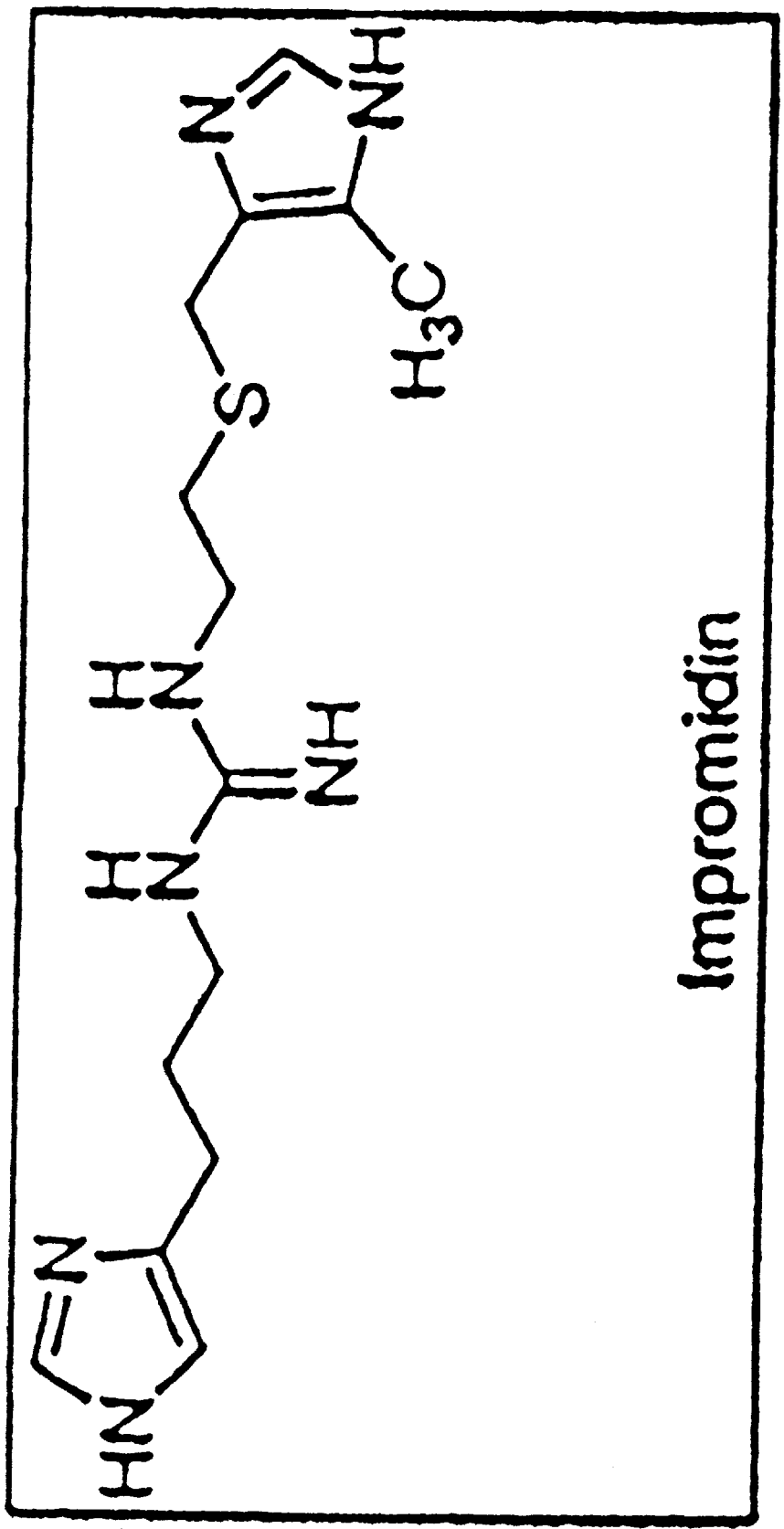
FIG. 1 illustrates a representative example of a guanidine-containing molecule, which is of interest in the area of pharmaceutical chemistry.

The present invention provides guanidinoglycosides that are useful as therapeutics for a number of diseases and disorders including, for example, viral infections (e.g., retroviral infections associated with HIV, HBV, and the like), bacterial infections, and disorders associated with, for example, inappropriate mitogenic signaling, non-insulin-dependent diabetes, and inhibition of enzymes including thrombin, glycosidases, and nitric oxide synthases.

The diprotected guanidinylation reagents disclosed herein (e.g., N,N'-diBoc-N''-triflylguanidine) are useful to efficiently convert multiamine-containing glycosides including, for example, kanamycin A and B, tobramycin, paromomycin, and neomycin B to the corresponding fully guanidinylated analogues (guanidinoglycosides). This transformation occurs in the presence of $H_2O$ under mild conditions. Guanidinotobramycin and guanidinoneomycin B were found to inhibit the replication of the HIV virus with activities approximately 100 times greater than the parent aminoglycosides.

The guanidinium group plays a key role at many RNA-protein binding interfaces, including the complexes formed between transcriptional elongation factors with mRNA, tRNA synthetases with tRNAs, ribosomal proteins with rRNA, and viral regulatory proteins with their cognate RNA binding sites. In contrast to ammonium groups, guanidinium groups are highly basic, planar, and exhibit directionality in their H-bonding interactions. The RNA affinity and selectivity of aminoglycoside-based ligands can be increased by replacing the ammonium groups with guanidinium groups. The present invention thus provides a new family of RNA ligands, termed "guanidinoglycosides", in which all of the ammonium groups of the natural aminoglycoside antibiotics have been converted into guanidinium groups (Schemes 9a and 9b below).

The term "alkyl" used herein refers to a monovalent straight or branched chain radical of from one to ten carbon atoms, including, but not limited to methyl, ethyl, n-propyl, isopropyl, n-butyl, isobutyl, tert-butyl, n-hexyl, and the like. Alkyl also represents cyclic radicals, including, but not limited to cyclopropyl, cyclobutyl, cyclopentyl, cyclohexyl, and the like.

The term "perfluoroalkyl" as used herein refers to a monovalent straight chain radical of from one to four carbon atoms, in which all hydrogen atoms are substituted by fluorine. A typical perfluorinated alkyl group is the trifluoromethyl group.

The term "aryl" when used alone refers to an aromatic radical whether or not fused. Preferred aryl groups include phenyl, naphthyl, biphenyl and the like. Aryl also refers to heteroaromatic groups including, but not limited to, furanyl, pyrrolyl, thienyl, pyrazolyl, thiazolyl, oxazolyl, pyridyl, pyrimidinyl, indolyl, and the like.

The term "substituted aryl" denotes an aryl group substituted with one, two or three substituents chosen from halogen, cyano, nitro, $C_1$–$C_{10}$ alkyl, $C_1$–$C_{10}$-alkoxy, trifluoromethyl, alkoxycarbonyl, and the like. Examples of such groups are 4-chlorophenyl, 2-methylphenyl, and 3-ethoxyphenyl.

The term "arylalkyl" means one, two or three aryl groups having the designated number of carbons, appended to an alkyl chain having the number of carbons designated. A typical arylalkyl group is the benzyl group.

The term "alkenyl" refers to a straight or branched chain group of from two to ten carbon atoms containing a carbon-carbon double bond, including, but not limited to allyl, vinyl, and the like.

Also, solid supported materials, such as cation exchange resins, including materials such as sulfonated polystyrene resin may be useful.

The guanidinylating reagents disclosed below are useful in the synthesis of the guanidinoglycosides. Such reagents overcome many of the difficulties, problems and environmental risks associated with previous guanidine synthesis methodologies. The guanidinylating reagent of the invention, when allowed to react with primary or secondary amines form alkylated guanidines, in high yields and high purities. The reaction conditions are mild and environmentally sound. One advantage over existing methods is that reaction conditions are mild and environmentally acceptable. All reagents utilized in the overall reaction schemes are inexpensive and non-toxic. The side products and waste display a low potential threat to the environment and can be disposed using normal precautions.

The compositions and methods provided herein are useful in the synthesis and transformation of amino functional groups into guanidine moieties, for example. Transformation of an amino functional group into a guanidine moiety is of great interest in many research efforts. Although progress has been made, many difficulties remain in the transformation of an amine to a guanidine structure. These difficulties are especially prevalent in solid-phase organic chemistry.

Guanidinylating reagent compounds of type I comprise guanidines with two protecting groups (P) and have the general structure:

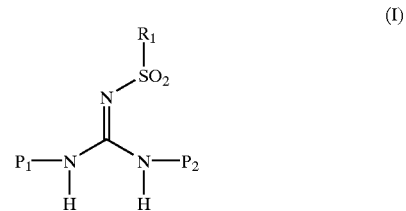

(I)

Preferably, $P_1$ and/or $P_2$ is Boc or Cbz and $R_1$ is phenyl, 4-methylphenyl, methyl, or trifluoromethyl. Analogs with other protecting groups such as Troc, Alloc or Moz at the P-position are expected to show the same kind of reaction. Because of the exceptionally strong electron-withdrawing character of the triflyl group, the triflyl-guanidines ($R_1$= trifluoromethyl) are the most reactive among the compounds synthesized so far and these are therefore preferred (see, for example, formula II). They have been shown to be superior to previously described guanidinylating reagents.

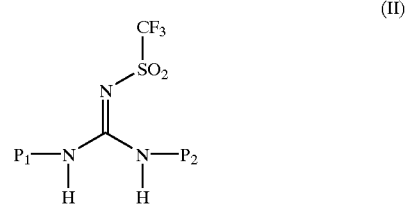

(II)

In addition, guanidinylating reagents having guanidines with three symmetrically arranged electron-withdrawing protecting groups (P) and have the structure

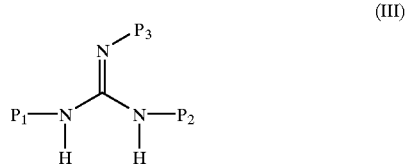

(III)

wherein $P_1$, $P_2$ and $P_3$ are the same or different urethane protecting groups, each having the general structure

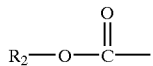

wherein $R_2$ is a substituted or unsubstituted alkyl or aryl group or heterocyclic group, can also be used in the synthesis of guanidinylated glycosides provided that the tri-protected reagents proceeds through a Mitsunobu reaction, as described below.

P, as used above, is chosen from urethane protecting groups which are conveniently removable. These groups are available in a large number of variations. Reviews of urethane groups and their use in peptide synthesis are provided by Geiger, R. and Konig, W. in "The Peptides" (Gross, E. Meienhofer, J., eds) Vol.3, p3. New York, N.Y. 1981 and in Wunsch, E. Methoden der Org. Chem. (Houben-Weyl) Vol. 15/1 (Wunsch, E.,ed.), p.46, Stuttgart: Thieme 1974. Particularly preferred are the urethane groups containing a substituted or unsubstituted benzylic carbon atom. Urethane-type protecting groups having a benzylic carbon atom are described by Bodanszky, M. (1984) Principles of Peptide Synthesis Chap. III Sec. C, Springer-Verlag, New York 1984. Such groups are removable by hydrogenolysis and by acidolysis, as well as by base-induced β-elimination. Preferably, the protecting group P is an alkyloxylcarbonyl group such as Boc (P=tert-butyloxycarbonyl), Cbz (P=benzyloxycarbonyl), Alloc (P=allyloxycarbonyl), Troc (P=2,2,2-trichloroethyloxycarbonyl), or Moz (P=4-methoxybenzyloxycarbonyl). The protecting groups Boc and Cbz are particularly preferred. Accordingly, as used herein "diprotected" denotes a compound having two protecting groups and "tri-protected" denotes a compound having three protecting groups.

Other guanidinylating reagents commonly used in the same manner as outlined in herein include the compounds below.

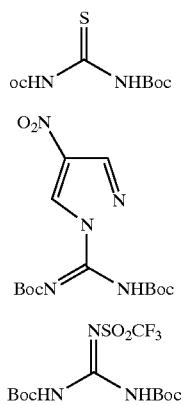

Guanidinylating reagent (II) has been successfully utilized in solution and on solid support. It rapidly reacts with alkyl and aryl amines without additional activating reagents and thus is the reagent of choice for the transformation of amines into guanidines in solution. Reagent (IV) is useful as a guanidinylating reagent when reacted with a Mukayama reagent.

The protected type III guanidines are weak acids and can be used to guanidinylate primary or secondary alcohols in a Mitsunobu-reaction to produce triprotected alkyl guanidines (scheme 4). The product of such a reaction still possesses one acidic hydrogen atom which can be exploited in a second Mitsunobu-reaction to produce protected dialkylated guanidines.

Scheme 4

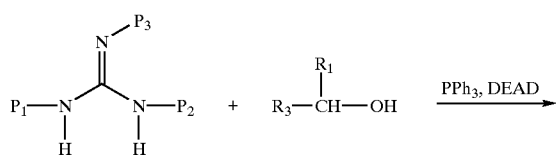

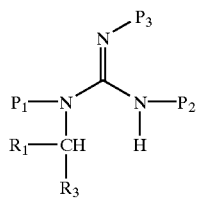

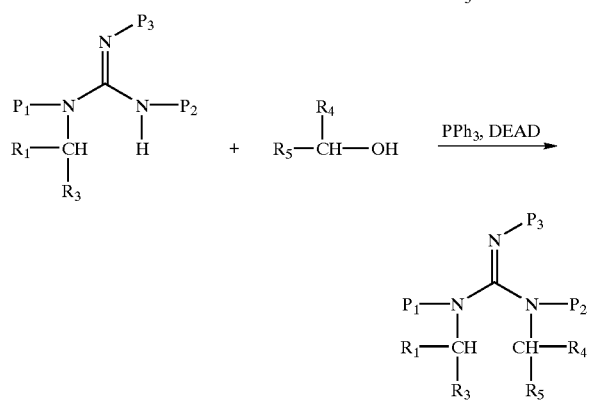

$R_1$, $R_3$, $R_4$, and $R_5$ can be hydrogen or any substituted or unsubstituted alkyl, alkenyl, aryl, or arylalkyl group as described earlier. $R_1$ and $R_3$ (and/or $R_4$ and $R_5$) may be part of a ring structure as in cyclopropanol, cyclobutanol, cyclopentanol, cyclohexanol and the like.

Compounds of type I, as described above, comprise guanidines with a sulfonyl group in addition to two urethane protecting groups, having the structure

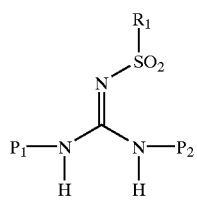

wherein $P_1$ and $P_2$ are as defined above and $R_1$ is a substituted or unsubstituted alkyl or aryl group. Perfluoroalkyl groups are preferred. Type II protected guanidines react with primary or secondary amines to produce diprotected alkyl guanidines (scheme 5).

Scheme 5

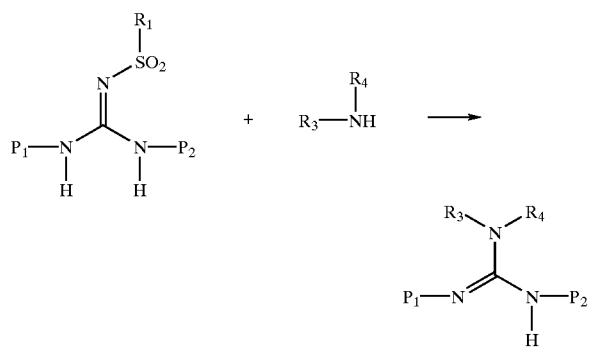

$R_3$ and $R_4$ can be hydrogen or any substituted or unsubstituted alkyl, alkenyl, aryl, or arylalkyl group as described earlier. $R_3$ and $R_4$ may be part of a ring structure as in aziridine, azetidine, pyrrolidine, piperidine, morpholine, and the like. Preferably, $P_1$ and/or $P_2$ is Boc or Cbz and $R_1$ is phenyl, 4-methylphenyl, methyl, or trifluoromethyl. Analogs with other protecting groups such as Troc, Alloc or Moz at the P-position are expected to show the same kind of reaction. Because of the exceptionally strong electron-withdrawing character of the triflyl group, the triflyl-guanidines ($R_1$=trifluoromethyl) are the most reactive among the compounds synthesized so far and these are therefore preferred. They have been shown to be superior to previously described guanidinylating reagents.

A general route towards symmetrical trisubstituted guanidines is described in U.S. Pat. No. 6,072,075, the disclosure of which is incorporated herein by reference in its entirety. The introduction of the first two protecting groups into guanidine hydrochloride is accomplished in one step. Yields between 50 and 80% are usually obtained. The diprotected guanidine is then treated with two equivalents of sodium hydride under anhydrous conditions. Acylation of the resulting anion then completes the synthesis.

Alternatively, symmetrical triprotected guanidines can be synthesized in one step from guanidine hydrochloride by phase transfer catalysis.

Guanidinylation agents of type II can be synthesized by deprotonation of diprotected guanidines with sodium hydride in an inert solvent and reaction of the resulting anion with a sulfonyl chloride. This method was successfully applied in the synthesis of N-,N'-di-Cbz-N"-methylsulfonyl-guanidine (R=benzyl, R'=methyl), N-,N'-di-Cbz-N"-phenylsulfonyl-guanidine (R=benzyl, R'=phenyl), and N-,N'-di-Cbz-N"-tosyl-guanidine (R=benzyl, R'=tosyl) as shown below.

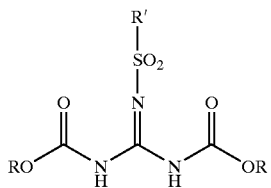

Instead of sulfonyl chlorides, sulfonyl anhydrides can be used in the synthesis of N-, N'-di-Cbz-N"-triflyl-guanidine.

In some cases triethylamine can be used as a base instead of sodium hydride. An example is the synthesis of N-,N'-di-Boc-N"-triflyl-guanidine.

Guanidinylation reagents of type III react with primary and secondary alcohols in a Mitsunobu-reaction to produce protected alkylated guanidines. This is exemplified in the synthesis of several orthogonally protected arginine analogs from suitable precursor molecules. The reactions with N-,N'-,N"-tri-Boc-guanidine are preferably carried out in refluxing THF and yields of up to 70% can be obtained. If N-,N',N"-tri-Cbz-guanidine is used as the guanidinylating species, the reaction can be carried out at room temperature. In addition, the yields are usually somewhat higher (up to 86%) than in comparable reactions with N-,N'-,N"-tri-Boc-guanidine.

Many biologically interesting guanidines contain two different alkyl substituents connected to two different N-atoms of the guanidine nucleus. Compounds of this type are accessible from triprotected guanidines by two consecutive Mitsunobu-reactions. An example is the synthesis of protected derivative of θ-methyl-arginine, an important inhibitor of nitric oxide synthetase.

N-,N'-Di-Boc-N"-triflyl-guanidine reacts rapidly and under mild conditions with primary and secondary amines. The reactions are carried out at room temperature and are usually complete within 1 h. Successful guanidinylation reactions have been performed in a wide range of solvents such as benzene, chloroform, or dichloromethane, acetonitrile or DMSO. Unpolar solvents such as benzene, chloroform, or dichloromethane are preferred. Compounds that are insoluble in one of the preferred solvents can in many cases be converted into a more soluble derivative which can then be successfully guanidinylated. This is demonstrated with the synthesis of a homoarginine derivative from N-α-Fmoc-lysine. In this procedure N-α-Fmoc-lysine is first silylated with MSTFA (N-methyl-N-trimethylsilyl-trifluoroacetamide) to generate a derivative that is soluble in dichloromethane. This derivative is then guanidinylated in the same pot with N-,N'-di-Boc-N"-triflyl-guanidine. The silyl-groups used to solubilize the starting material are removed again during the workup procedure. Other protected diamino acids such as Nα-Fmoc-ornithine, N-α-Fmoc-2,4-diamino-butyric acid or N-α-Fmoc-2,3-diamino-propionic acid are expected to show the same kind of reaction. The arginine analogues produced by this methodology are orthogonally protected and can be used for peptide coupling reactions without further modifications.

Exceptionally good yields of protected guanidines are obtained by guanidinylation of secondary amines. Even with secondary amines such as piperazine the reaction is extremely facile.

N-,N'-Di-Cbz-N"-triflyl-guanidine is an excellent reagent for the guanidinylation of unreactive aromatic amines. The reaction with aniline is complete after 1 h at room temperature.

Reactions on solid phase are usually slower than comparable reactions in solution. Much effort is currently directed to adapt useful chemical reactions to the unique conditions of solid phase synthesis. Such optimized reactions are especially important for the construction of chemical libraries by parallel and combinatorial methods.

The high reactivity of N-,N'-di-Boc-N"-triflyl-guanidine allows guanidinylations on solid phase to be performed successfully. This is demonstrated by the conversion of an ornithine residue in a peptide sequence to arginine. The peptide was assembled on a PAM-resin (PAM: phenylacetamidomethyl) by standard methods. Ornithine, the ε-amino group protected by Fmoc, was incorporated in place of arginine. After complete assembly of the sequence the Fmoc-group on the ornithine side chain was removed selectively and the free amino group was guanidinylated with N-,N'-di-Boc-N"-triflyl-guanidine. The unprotected arginine-containing peptide was then obtained after removal of the Boc-groups and cleavage of the peptide from the resin with HF. Analysis of the crude peptide by FAB-MS indicated a homogeneous product. No peaks suggesting incomplete guanidinylation could be detected.

The guanidinylation of benzylamine in benzene was chosen as a model reaction to compare two commercially available guanidinylating agents with N-,N'-di-Boc-N"-triflyl-guanidine. All three reactions were carried out in an NMR-instrument and the formation of product was followed by integration of the signals of the benzylic $CH_2$-groups. Under the conditions chosen, N-,N'-di-Boc-N"-triflyl-guanidine proved superior to the other reagents. Similar results were obtained in deuterated chloroform and in deuterated acetonitrile.

Transformation of an amino functional group into a guanidine moiety is a great interest in chemical research. FIG. 1 illustrates a representative example of a guanidine-containing molecule, which is of interest in the area of pharmaceutical chemistry. Impromidin is a potent and selective histamine-$H_2$-receptor agonist and attempts have been made to improve its potency by variation of the substituents on the guanidine core.

Figure 2:
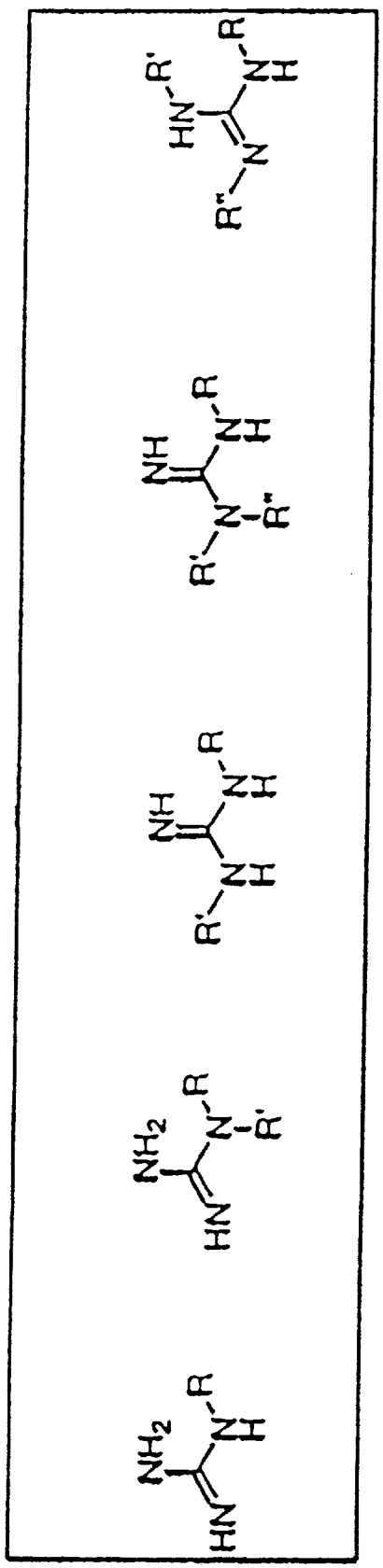
FIG. 2 depicts all possible substitution patterns on the guanidine core that are accessible through the guanidinylating reagents of the invention.

The guanidinylating reagent of the present invention provides rapid access to a wide variety of alkylated guanidines. Accordingly, the present invention provides the ability to introduce a substituent onto each of the nitrogen atoms of a guanidine core. FIG. 2 depicts all possible substitution patterns on the guanidine core that are accessible through the present invention. Since a wide variety of guanidines are accessible with one reagent, the present invention provides the ability to synthesize a diverse library of guanidines-based compounds.

Scheme 6 and 7 depict to methods for the guanidinylation of an aminoglycoside. Preferably, Scheme 7 is used. Guanidinylation of the aminoglycosides was developed commencing with glucosamine hydrochloride (2a). Guanidinylated glucosamine (2b) was prepared by treatment of glucosamine hydrochloride (2a) with a methanolic solution of NaOMe followed by $NEt_3$ and N,N'-diBoc-N''-triflylguanidine (II) in 94% yield. The Boc protecting groups were easily removed using a mixture of $TFA/CH_2Cl_2$ (1:1) providing compound 2c in good yield.

Scheme 6

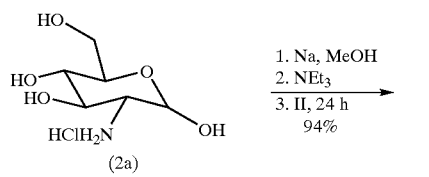

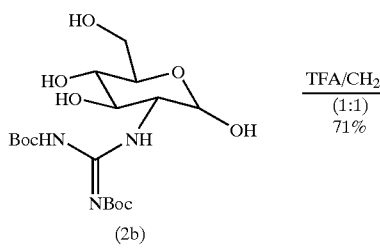

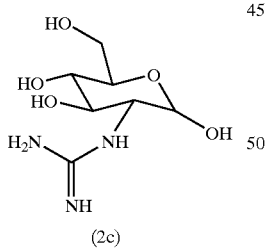

2-Doexystreptamine (3a, 2-DOS) is the cyclitol core unit of many aminoglycoside antibiotics. When the dihydrobromide salt of 2-DOS was subjected to methanolic NaOMe, the free diamine precipitated from the solution, which prevented any reaction with reagent II. When the reaction mixture was heated at reflux, only diBoc-guanidine was obtained. A variety of solvents (DMSO, DMF, MeOH) were examined for the conversion of compound 3a to compound 3b in the presence of reagent II and $NEt_3$. It was recognized that polar solvents slow the rate of guanidinylation. Polar solvents mixed with water increased the solubilization of the aminoglycoside and thus the efficiency of reaction. Thus, 1,4-dioxane and water completely solubilized the aminoglycoside. Other combinations of polar solvents and water will be apparent to those of skill in the art, such solvents including, for example, dimethylsulfoxide (DMSO) and water. The guanidinylation of diamine 3a with reagent II not only tolerated the addition of $H_2O$ but worked efficiently yielding 70% of the target compound 3b. Subsequent deprotection using TFA resulting in an 87% yield of compound 3c (Scheme 7). Various ratios of the polar solvent and water can be empirically determined. For example, the ratio of such solvents can include 3:1, and 4:1 where 1,4-dioxane and water is used (e.g., Schemes 7 and 8).

Scheme 7

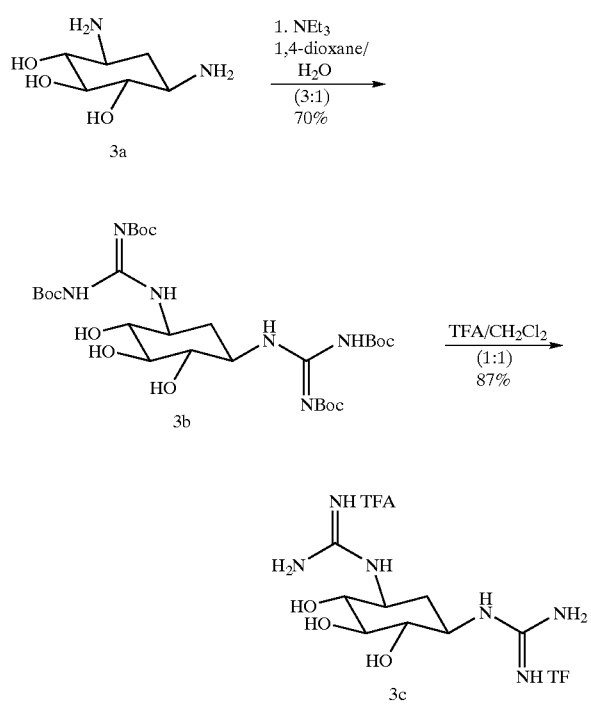

The methods and compositions of the invention allow for the efficient guanidinylation of aminoglycosides in an aqueous media. For example, Scheme 8 shows the guanidinylation of tobramycin using N,N'-diBoc-N''-triflylguanidine:

Scheme 8

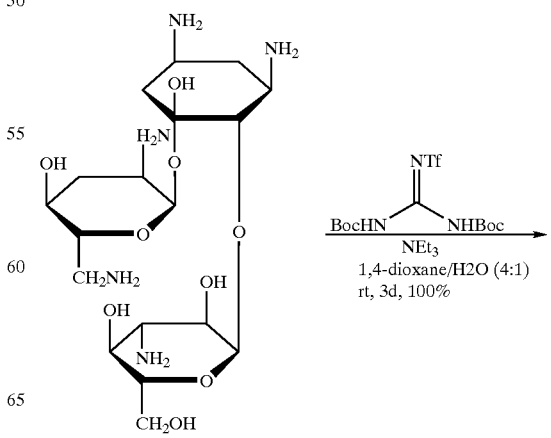

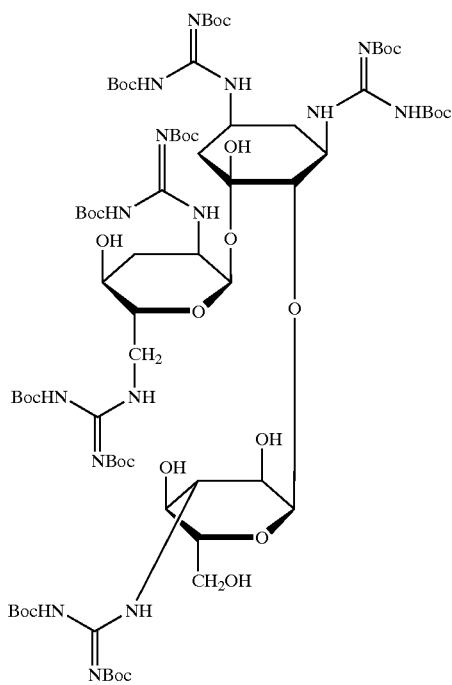

Tobramycin was fully guandinylated using 15 equivalents of N,N'-diBoc-N"-triflylguandine in aqueous media to provide the guanidinylated-Boc protected tobramycin in quantitative yield (Scheme 8). The Boc protecting groups were easily removed in 99% yield using TFA without affecting the stereochemistry. Table 1 and Scheme 9a and 9b below show the preparation and deprotection of guanidinoglycosides from other aminoglycosides employing similar conditions to those for tobramycin. The resulting guanidinoglycosides have shown promising results as antiviral agents using the solid-phase assay described below.

TABLE 1

Preparation and deprotection of guanidinoglycosides.

| amino-glycoside | No. of amines | Eq. of 1 | Yield (%) | FAB-MS (M + H+) | Deprot. Conditions | Deprot Yield (%) |
|---|---|---|---|---|---|---|
| glucos-amine[a] | 1 | 1.1 | 82 | 422 | SnCl$_4$[4] | 89 |
| 2-deoxy-strept-amine[b] | 2 | 2.1 | 70 | 647 | SnCl$_4$ | 97 |
| Kanamycin[b] | 4 | 8 | 80–91 | 1454 | TFA/CH$_2$Cl$_2$ | 100 |
| tobramycin[b] | 5 | 15 | 100 | 1678 | TFA/CH$_2$Cl$_2$ | 99 |
| neomycin | 6 | 18 | 68–70 | 2066 | TFA/CH$_2$Cl$_2$ | 100 |
| paromo-mycin[b] | 5 | 15 | 68 | 1825 | TFA/CH$_2$Cl$_2$ | 92 |

[a]Reaction carried out in MeOH for 2 d with equimolar NEt$_3$ as 1.
[b]Reaction carried out in 4:1 mixture of 1,4-dioxane/H$_2$O for 3 d with equimolar NEt$_3$ as 1.
[c]Reaction carried out in 4:1 mixture of 1,4-dioxane/H$_2$O for 7 d with equimolar NEt$_3$ as 1.

Scheme 9a:

|  | R$_1$ | R$_2$ |
|---|---|---|
| Kanamycin A | OH | H |
| Guanidino Kanamycin A | OH | (C=NH)NH$_2$ |
| Kanamycin B | NH$_2$ | H |
| Guanidino Kanamycin B | NH(C=NH)NH$_2$ | (C—NH)NH$_2$ |

Scheme 9b:

|  | R$_1$ | R$_2$ |
|---|---|---|
| Paromomycin | OH | H |
| Guanidino Paromomycin | OH | (C=NH)NH$_2$ |
| Neomycin | NH$_2$ | H |
| Guanidino Neomycin | NH(C=NH)NH$_2$ | (C=NH)NH$_2$ |

The family of guanidinoglycosides have an enhanced affinity and selectivity to the HIV-1 Rev-Response Element. Binding between the Rev polypeptide and the Rev-responsive element (RRE) in HIV is described in Heaphy et al. (1991) Proc. Natl. Acad. Sci. USA 88:7366–7370; Bartel et al. (1992) Proc. Natl. Acad. Sci. USA 89:758–762. Binding between a 17 amino acid peptide corresponding to residues 34–50 of Rev was shown in Kjems et al. (1991) Cell 67:169–178 and (1992) EMBO J. 11:1119–1129. Inhibition of binding between Rev and RRE as a therapy for HIV-1 infection is proposed in, e.g., Rosen (1992) J. Virol. 66:600–607. Therapeutic strategies for HIV-1 infection are proposed in the following published PCT patent applications: WO92/07871; WO92/05195; and WO91/10453. The expression of the Rev protein of HIV-1 in Drosophila cells is described in WO92/06212.

Figure 3:
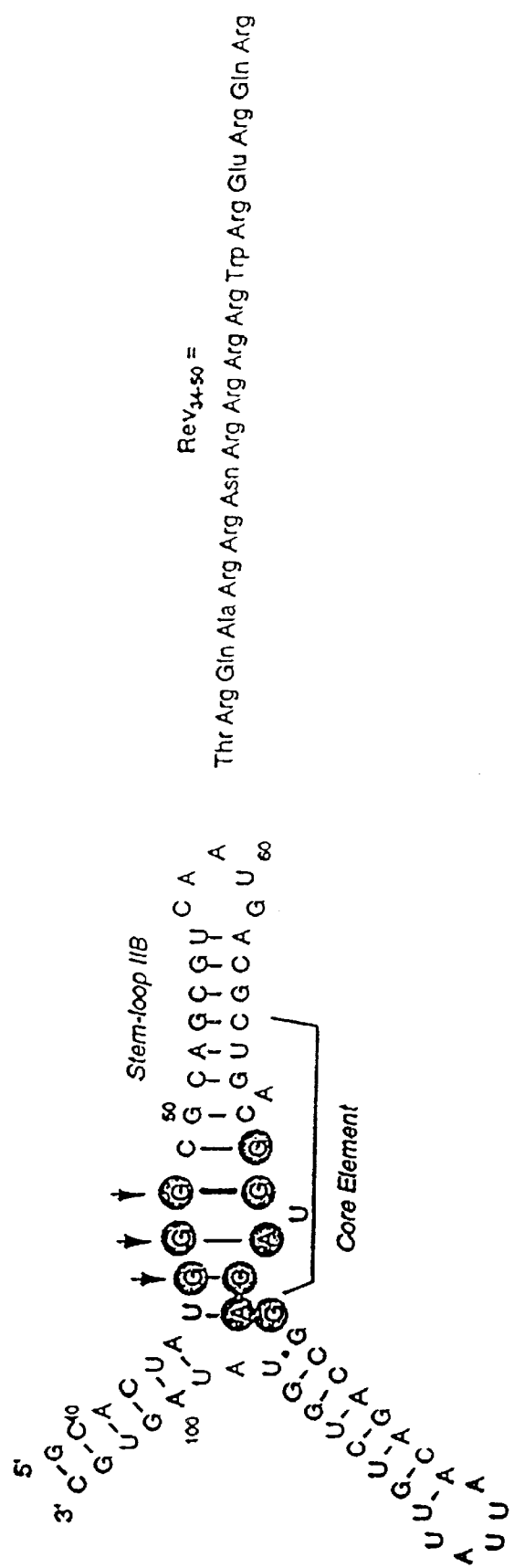
FIG. 3 depicts Domain II of the HIV RNA. Vertical lines indicate base pairing within the RRE core element. The unique G48:G71 base pair is bolded. A summary of the chemical protection by Rev and neomycin B on the proposed secondary structure of the 67 nt RNA that contains bases 38–104 of the RRE is shown. The aminoglycosides protect three consecutive G's (46–48) that are also strongly protected by the Rev protein.

Recent studies have demonstrated that aminoglycoside antibiotics competitively block the binding of the HIV-1 Rev protein to its RNA recognition element (RRE), thereby inhibiting the production of the virus (FIG. 3). While this example provides an important precedent for the utilization of small molecules to target viral RNA sites, the natural aminoglycoside antibiotics are toxic and lack site-specificity. The substitution of some or all of the ammonium groups on the aminoglycosides by guanidinium groups will provide new small molecules with high affinity and specificity to the HIV-1 RRE site. The reagents and methods described herein allow for the substitution and development of such substituted amino glycosides.

In one embodiment, the present invention provides a method for treating a subject having a bacterial or viral infection or treating a subject susceptible to infection with a bacteria or virus. The method includes administering a guanidinoglycoside of the invention, an analogue, derivative, or salt thereof, prior to, simultaneously with, or subsequent to infection by a bacteria or viral organism.

In another embodiment, the invention provides a method of inhibiting or modulating the progression of viral infections (e.g., retroviral infections associated with HIV, HBV, and the like), bacterial infections, and disorders associated with, for example, inappropriate mitogenic signaling, non-insulin-dependent diabetes, and inhibition of disorders associated with thrombin, glycosidases, and nitric oxide synthases.

Thus, the guanidinoglycosides of the present invention, as well as analogues, derivatives, or salts thereof are useful in the treatment of bacterial or viral infections in general, either separately or in combination with other antibiotic or antiviral agents. These compounds may be administered orally, topically or parenterally in dosage unit formulations containing conventional non-toxic pharmaceutically acceptable carriers, adjuvants, and vehicles. The term parenteral as used herein includes subcutaneous injections, aerosol, intravenous, intramuscular, intrathecal, intracranial, intrastemal injection or infusion techniques.

The present invention also has the objective of providing suitable topical, oral, and parenteral pharmaceutical formulations for use in the treatment of bacterial and viral infections. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. The tablets contain the acting ingredient in admixture with non-toxic pharmaceutically acceptable excipients which are suitable for the manufacture of tablets. These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

The guanidinoglycoside compounds of the invention (including analogues, derivatives, or salts thereof) can be administered, for in vivo application, parenterally by injection or by gradual perfusion over time independently or together. Administration may be intravenously, intraperitoneally, intramuscularly, subcutaneously, intracavity, or transdermally. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, growth factors and inert gases and the like.

To facilitate the discovery of active guanidinoglycosides an assay system using HIV-1 response elements can be used. For example, RRE-specific binders as well as TAR specific binders can be identified using the methods of the present invention. The present invention provides a rapid screening assay and method depicted in FIG. 4. The Rev-RRE assay relies on the release of a fluorescently tagged Rev fragment from an immobilized RRE-Rev complex and can be performed under various stringency levels. The assay can be conducted in the presence of competing RNA molecules, other potential cellular targets, or cellular extracts. Only high affinity ligands can effectively compete with the bound $Rev_{34-50}$ peptide ($K_d$ is approximately 1 nM), thus releasing the highly fluorescent molecules into solution. Non-selective binders will be scavenged by competitor molecules present in solution. Only when a highly selective RRE binder is present will a positive fluorescent signal be elicited in solution.

Figure 4:
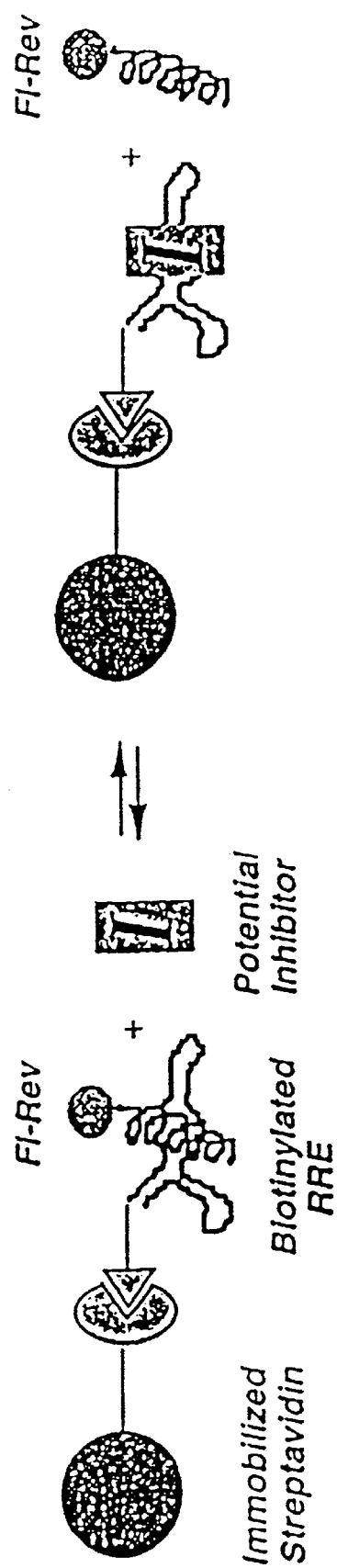
FIG. 4 is a schematic illustration of an assay system of the invention.

In one embodiment, the present invention provides an assay for identifying a test compound which binds to RRE. The assay includes an immobilized RRE, a detectably labeled Rev, and a test compound. A test compound that liberates the labeled Rev due to competitive binding to the RRE results in an increase in the labeled Rev in the supernatant of the assay. Accordingly, following incubation of immobilized RRE, a labeled Rev, and a test compound, the supernatant is measured and the amount of label in the supernatant is determined. The amount of label in the supernatant is indicative of the degree or ability of the test compound to bind to the RRE or REV polypeptide. By comparing the amount of label in the supernatant with the amount in a control or standard sample, one can identify a test compound which effectively competes with the Rev for binding to RRE. FIG. 4 shows a schematic representation of one embodiment of the assay. In the depicted embodiment of FIG. 4 the ternary complex containing a fluorescently tagged Rev peptide bound to an immobilized RRE is incubated with the test compound (e.g., a potential competitor, binding agent or inhibitor)under conditions and in the presence of competing RNA molecules n a microcentrifuge filter tube. After incubation, the mixture is filtered and the filtrate is illuminated. In the presence of a strong and selective RRE binder, the fluorescently labeled peptide will be released from the beads into solution and the filtrate will become fluorescent.

The RRE can be effectively immobilized to a solid support by any number of techniques known in the art. For example, a tag is covalently linked to the RRE and the tag is then bound to a tag-binding molecule attached to a solid support, thereby effectively binding the RRE to the solid support. The tag can be any of a variety of components. In general, a molecule which binds the tag (a tag binder) is fixed to a solid support, and the tagged nucleic acid (e.g., the RRE) is attached to the solid support by interaction of the tag and the tag binder. A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fe region of an immunoglobulin, and the like).

The solid support may be any material known to those of ordinary skill in the art to which a tag-binder may be attached, such as a test well in a microtiter plate, a nitrocellulose filter or another suitable membrane. Alternatively, the support may be a bead or disc, such as glass, fiberglass, latex, polymers, metals, metalloids, ceramics, organics, or a plastic such as polystyrene or polyvinylchloride.

The Rev may be labeled with any number of detectable molecules. The labels in the present invention can be primary labels (where the label comprises an element which is detected directly) or secondary labels (where the detected label binds to a primary label, e.g., as is common in immunological labeling). An introduction to labels, labeling procedures and detection of labels is found in Polak and Van Noorden (1997) Introduction to Immunocytochemistry second edition, Springer Verlag, N.Y. and in Haugland (1996) Handbook of Fluorescent Probes and Research Chemicals a combined handbook and catalogue Published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodintine isothiocynate (TRITC), and the like), dixogenin, biotin, phycoerythrin, AMCA, CyDyes™, and the like), radiolabels (e.g., $^3$H, $^{125}$I, $^{35}$S, $^{14}$C, $^{32}$P, $^{33}$P, and the like), enzymes (e.g., horse-radish peroxidase, alkaline phosphatase, and the like) spectral calorimetric labels such as colloidal gold or colored glass or plastic (e.g., polystyrene, polypropylene, latex, and the like) beads. The label may be coupled directly or indirectly to Rev according to methods well known in the art. As indicated above, a wide variety of labels may be used, with the choice of label depending on sensitivity required, ease of conjugation with the compound, stability requirements, available instrumentation, and disposal provisions. In general, a detector is adapted to the particular label which is used. Typical detectors include spectrophotometers, phototubes and photodiodes, microscopes, scintillation counters, cameras, film and the like, as well as combinations thereof. Examples of suitable detectors are widely available from a variety of commercial sources known to persons of skill.

Preferred labels include those which utilize 1) chemiluminescence (using horseradish peroxidase and/or alkaline phosphatase with substrates that produce photons as breakdown products) with kits being available, e.g., from Molecular Probes, Amersham, Boehringer-Mannhiem and Life Technologies/Gibco BRL; 2) color production (using both horseradish peroxidase and/or alkaline phosphatase with substrates that produce a colored precipitate; kits available from Life Technologies/Gibco BRL, and Boehringer-Mannheim); 3) hemifluorescence using, e.g., alkaline phosphatase and the substrate AttoPhos (Amersham) or other substrates that produce fluorescent products, 4) Fluorescence (e.g., using Cy-5 (Amersham), fluorescein, and other fluorescent tags); and 5) radioactivity. Other methods for labeling and detection will be readily apparent to one skilled in the art.

Fluorescent labels are highly preferred labels, having the advantage of requiring fewer precautions in handling, and being amendable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Fluorescent moieties, which are incorporated into the labels of the invention, are generally known, including Texas red, dixogenin, biotin, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes, flavin and many others. Many fluorescent tags are commercially available from the SIGMA chemical company (Saint Louis, Mo.), Molecular Probes, R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.), as well as many other commercial sources known to one of skill.

The basic principle of the assay systems used to identify compounds that inhibit binding of Rev to RRE or compounds that interact with RRE involves preparing a reaction mixture containing the target (e.g., RRE) and the binding partner (e.g., labeled-Rev) under conditions and for a time sufficient to allow the two to interact and bind, thus form a complex. In order to test a compound for inhibitory activity, the reaction mixture is prepared in the presence and absence of the test compound. The test compound can be initially included in the reaction mixture, or can be added at a time subsequent to the addition of the RRE and its binding partner, Rev. Control reaction mixtures are incubated without the test compound or with a placebo. The presence of labeled-Rev that is not bound to RRE over that amount found in a control or standard sample is indicative of a test compound that competes with Rev for binding to RRE.

The test compounds can include, but are not limited to, cellular proteins, peptides such as, for example, soluble peptides, including, but not limited to, Ig-tailed fusion peptides, comprising extracellular portions of target gene product transmembrane receptors, and members of random peptide libraries (see, e.g., Lam, K. S. et al., 1991, Nature 354:82–84; Houghten, R. et al., 1991, Nature 354:84–86) made of D-and/or L-configuration amino acids, phosphopeptides (including but not limited to members of random or partially degenerate, directed phosphopeptide libraries; see, e.g., Songyang, Z. et al., 1993, Cell 72:767–778), antibodies (including, but not limited to polyclonal, monoclonal, humanized, anti-idiotypic, chimeric or single chain antibodies, and Fab, F(ab')$_2$ and Fab expression library fragments, and epitope-binding fragments thereof), and small organic or inorganic molecules. In a preferred embodiment, the test molecule is a guanidinoglycoside (e.g., a guanidinylated tobramycin, guanidinylated glucosamine, guanidinylated kanamycin, guanidinylated neomycin, guanidinylated 2-deoxystreptamine).

Figure 5:
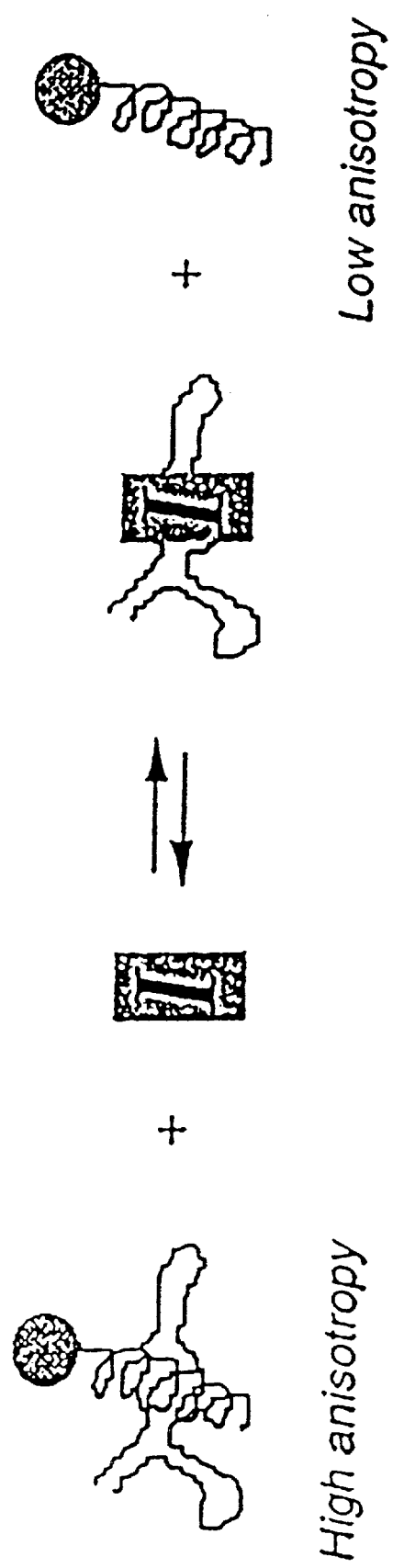
FIG. 5 is a schematic illustration of a fluorescence anistropy assay system of the invention.

In a modification of the above assay, the solid support aspect of the above embodiment is removed. The biophysical characteristics of potential inhibitory test compounds can be detected by fluorescence anisotropy as depicted in FIG. 5. The RRE-bound fluorescent peptide has a slower Brownian tumbling motion relative to the free peptide in solution. Upon displacement of the fluorescently labeled Rev from the RRE by a competing inhibitor, a decrease in the anisotropy value is observed. The displacement of the labeled-Rev can be followed by monitoring the anisotropy at the emission wavelength of the $Rev_{34-50}$-bound fluorophore.

Results obtained with the solid phase assay illustrates differences in affinity and specificity the RRE (Tables 2 and 3). One of skill in the art will recognize that the $IC_{50}$ values presented in Tables 2 and 3 are dependent upon the conditions used and will vary accordingly. As demonstrated below, the guanidinylated tobramycin product is about 20-fold more active when compared to tobramycin that has not been guanidinylated. Furthermore, unmodified tobramycin shows a significantly lower activity in the presence of tRNA, but guanidinylated tobramycin has approximately the same activity in the presence of both competing DNA and tRNA. This indicates a high degree of specificity for the RRE.

TABLE 2

$IC_{50}$ values derived from Solid Phase Assay.

| Compound | $IC_{50}$ | $IC_{50}$ with DNA | $IC_{50}$ with tRNA |
| --- | --- | --- | --- |
| Tobramycin | 50 uM | 55 uM | 110 uM |
| Guanidinylated Tobramycin | 2.5 uM | 3.0 uM | 3.5 uM |

TABLE 3

$IC_{50}$ values derived from Fluorescence Anisotropy.

| Glycoside | $IC_{50}$ (uM) amino form | $IC_{50}$ (uM) guandino form |
| --- | --- | --- |
| Neomycin B | 1.0 | 0.2 |
| Tobramycin | 10 | 0.65 |
| Kanamycin A | 100 | 8.0 |

Fluorescence anisotropy confirms an increase in inhibitory activity of all "guanidinoglycosides" when compared to their respective "amino" compounds. In all cases, guanidinylation of the parent aminoglycoside results in a compound with significantly higher inhibitory activity.

EXAMPLES

Unless otherwise noted, all materials were obtained from commercial suppliers and used without further purification. N,N'-DiBoc-N"-triflylguanidine was prepared as described above. $CH_2Cl_2$ and $CHCl_3$ were dried first with neutral alumina and $NEt_3$ with KOH and then distilled from $CaH_2$. Analytical thin-layer chromatography was carried out on precoated silica gel plates. Flash column chromatography was performed using silica gel (230–400 mesh). All NMR spectra were obtained on a 360 or a 400 MHz spectrometer. The purity of the new compounds was determined by NMR spectroscopy.

General Procedure A for the Guanidinylation of Aminoglycosides. To a solution of aminoglycoside (5 amines, 0.054 mmol) in $H_2$) (0.5 mL) was added 1,4-dioxane (2.5 mL) and N,N'-DiBoc-N"triflylguanidine (1, 0.82 mmol) in alternating portions so the solution remained relatively clear. After 5 min, $NEt_3$ (0.82 mmol) was added at room temperature. After 3–4 days, the 1,4-dioxane was removed under reduced pressure. The remaining residue and $H_2O$ was extracted with $CHCl_3$ (3×10 mL), washed with $H_2O$ and brine, and dried ($MgSO_4$). The fully guanidinylated product can be isolated by flash column chromatography (fcc) on silica gel ($CHCl_3$/MeOH).

General Procedure B for the Deprotection of Guanidinoglycosides. A solution of $TFA/CH_2Cl_2$ (1:1, 1 mL) was added to the protected guanidinoglycoside (0.041 mmol) at room temperature. After approximately 4 h, the solution was diluted with toluene, concentrated in vacuo, and dissolved in $H_2O$. Subsequent lyopholyzation of $H_2O$ provided the deprotected guanidinoglycoside as a fluffy white powder.

N-D-Glucosamine-N',N"-bis(tert-butoxycarbonyl) guanidine. A solution of NaOMe was prepared from Na metal (17.4 mg, 0.76 mmol) and MeOH (6 mL) at 0° C. Once the reaction was complete, D-glucosamine hydrochloride (163 mg, 0.76 mmol) was added in one portion, and the resulting mixture was allowed to warm to room temperature. After 20 min, $NEt_3$ (0.11 mL, 0.76 mmol) and reagent 1 (269 mg, 0.69 mmol) were added, and the mixture was allowed to stir overnight. The resulting mixture was concentrated under reduced pressure. The oily residue was purified by fcc ($CHCl_3$/ MeOH 95:5) to provide compound 2b (above) (300 mg, 94%) as an off-white foam: $^1H$ NMR ($CDCl_3$, 400 MHz, major diastereomer) ä 11.43 (br s, 1H), 8.71 (d, J) 7.6 Hz, 1H), 5.27 (d, J) 3.2 Hz, 1H), 4.21 (dd, J) 8.8, 8.8 Hz, 1H), 3.90–3.87 (m, 2H), 3.82–3.78 (m, 2H), 3.59–3.55 (m, 1H), 1.46 (s, 9H), 1.42 (s, 9H); $^{13}C$ NMR (CDCl3, 100 MHz, major diastereomer) ä 162.4, 156.9, 152.4, 91.1, 83.4, 79.7, 73.5, 71.4, 71.3, 61.7, 54.7, 28.2 (3C), 28.1 (3C); MS (FAB) m/z (rel intensity) 444 ([M+Na]+, 47), 422 ([M+H]+, 65); HRMS (FAB) m/z calcd for $C_{17}H_{31}N_3O_9$ $(M+H)^+$ 422.2139, found 422.2128, Δ=2.6 ppm.

D-Glucosamine-Guanidine Trifluoroacetate (2c). According to GPB, TFA/CH2Cl2 (1:1, 1 mL) and compound 2b (0.366 g, 0.869 mmol) provided 2c (0.207 mg, 71%): 1 H NMR (DMSO, 400 MHz, major diastereomer) ä 8.97 (s, 1H), 8.56 (s, 1H), 8.06 (s, 2H), 5.75 (d, J) 6.0 Hz, 1H), 4.43 (br s, 4H), 4.16 (d, J) 6.4 Hz, 1H), 4.09 (d, J) 2.0 Hz, 1H), 3.67 (ddd, J) 8.4, 5.2, 2.4 Hz, 1H), 3.54 (dd, J) 8.0, 2.4 Hz, 1H), 3.52 (dd, J) 5.6, 2.0 Hz, 1H), 3.35 (dd, J) 11.2, 5.2 Hz, 1H); 13 C NMR (DMSO, 100 MHz, major diastereomer) ä 158.1, 88.2, 79.6, 73.1, 67.9, 66.2, 63.5; MS (ESI-positive) m/z (rel intensity) 222 (55), 204 (100); HRMS (FAB) m/z calcd for $C_7H_{15}N_3O_5$ $(M+H)^+$ 222.1084, found 222.1088, Δ=1.8 ppm. The NMR spectra and mass spectrometry measurements for the additional guandinoglycosides disclosed herein were performed and provided similar structures as described herein (see also, Baker, et al., J. Org. Chem, 65:9054–9058, 2000, the disclosure of which is incorporated herein in its entirety).

Figure 6:
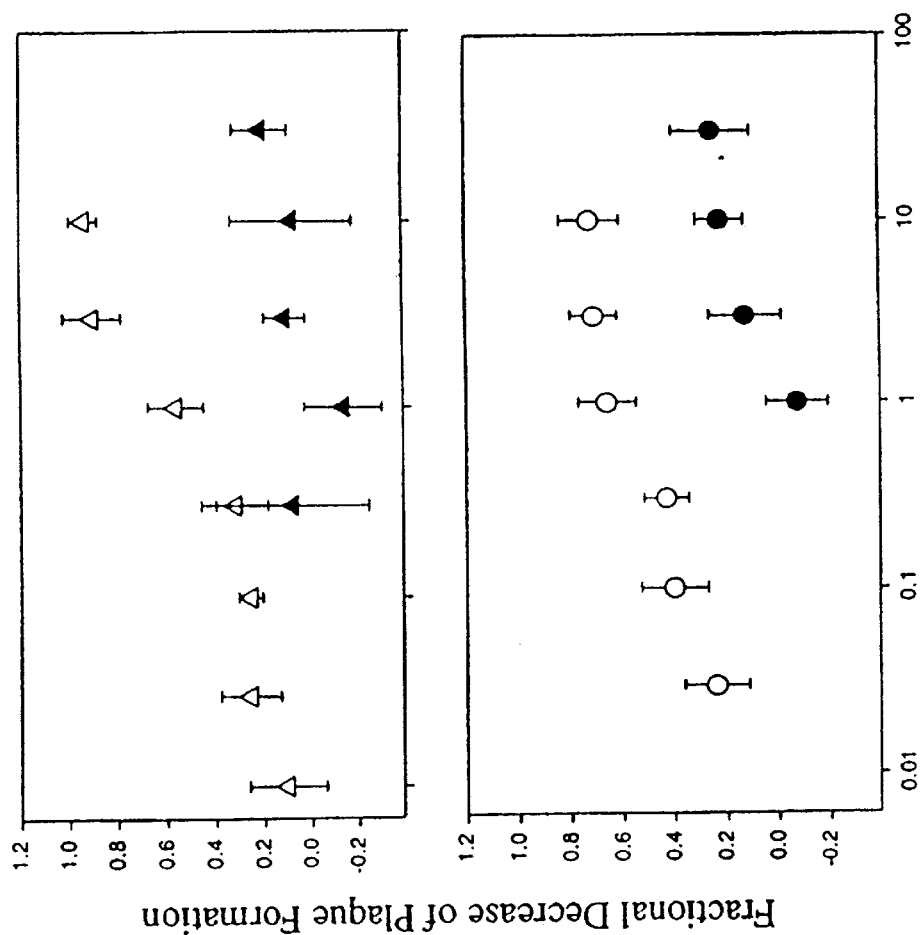
FIG. 6 shows the inhibition of HIV-1 replication in HeLa cells. Top panel shows tobramycin (closed triangles) and guanidinotobramycin (open triangles). Bottom panel shows neomycin B (closed circles) and guanidinoneomycin B (open circles).

It has been documented that guanidinosubstituted sugar-like compounds have been found to inhibit HIV replication. By converting aminoglycosides into guanidinoglycosides the biological activities of these glycosides were dramatically affected. Neomycin B was reported to be an in vivo and in vitro inhibitor of Rev-RRE binding, as well as an effective inhibitor of HIV-1 replication in vivo. The ability of guanidinoneomycin B and guanidinotobramycin to inhibit viral replication in HIV-1-infected CD4+ HeLa cells was measured and compared to the antiviral activities of neomycin B and tobramycin (FIG. 6). As evidenced by the dose-dependent decrease in plaque formation, the guanidinoglycosides inhibit HIV replication with activities approximately 100 times higher than their amino precursors (FIG. 6). The antiviral activity of the guanidinoglycosides may be related to their ability to bind the RRE with high affinity and specificity, thus preventing the HIV-1 Rev-RRE interaction and viral replication.

The HIV-1 Rev-RRE interaction was used to examine the impact of guanidinylation upon RNA binding, and to probe the potential antiviral activity of these compounds. The binding of Rev to the RRE (Rev response element) is responsible for the export of unspliced and singly spliced HIV genomic RNA out of the host nucleus. This essential protein-RNA interaction remains an important, and nonutilized, therapeutic target. The high-affinity Rev binding site on the RRE has been localized to the purine-rich bulge. The binding of Rev to the RRE is governed by the arginine-rich fragment, $Rev_{34-50}$. Key guanidinium groups make direct contacts with the RNA platform and are essential for the specific binding of Rev to the RRE. Fluorescence anisotropy has been employed to determine the affinity of the new derivatives to the RRE in solution. The RRE-bound fluorescent Rev peptide has a slower Brownian tumbling motion relative to the free peptide. Upon displacement of the fluorescein-labeled Rev peptide from the RRE by an inhibitor, a decrease in the anisotropy value is observed. Table 4 (column a) compares the $IC_{50}$ values of the guanidinoglycosides to the aminoglycosides. Guanidinylation of kanamycin A, kanamycin B, and tobramycin results in a greater than 10-fold increase in inhibitory activity relative to the parent compounds. A 5-fold increase in activity is observed upon guanidinylation of neomycin B and paromomycin.

TABLE 4

$IC_{50}$ Values (uM) as Determined by Fluorescence Anisotropy and Solid-Phase Assays

| glycoside | (a) Anisotropy | (b) Solid-Phase | (c) Solid-Phase + polyA polyU | (d) Solid-Phase + DNA | (e) Ratio (c)/(b) |
|---|---|---|---|---|---|
| KanamycinA | 750 | 700 | 1300 | 750 | 1.9 |
| guanidino-kanamycinA | 65 | 50 | 60 | 55 | 1.2 |
| KanamycinB | 80 | 80 | 160 | 90 | 2.0 |
| guanidino-kanamycinB | 3.5 | 3.0 | 4.7 | 3.5 | 1.6 |
| Tobramycin | 44 | 45 | 140 | 50 | 3.1 |
| guanidino-tobramycin | 3.8 | 3.0 | 5.0 | 3.5 | 1.7 |
| Paromomycin | 65 | 55 | 110 | 60 | 2.0 |
| guanidino-paromomycin | 18 | 14 | 20 | 16 | 1.4 |
| Neomycin B | 6.0 | 6.0 | 16 | 8.0 | 2.7 |
| guanidino-neomycin B | 1.3 | 0.8 | 4.5 | 0.9 | 5.6 |

A novel solid-phase assembly was used to evaluate the RNA specificity of the new derivatives. This assay relies on the displacement of a fluorescent Rev peptide from a solid-phase immobilized RRE and can be performed in the presence of competing nucleic acids. Table 4 (columns b–d) summarizes the $IC_{50}$ values determined by this method. By comparing $IC_{50}$ values measured in the absence of any competitors to the values measured in the presence of DNA or RNA, a quantitative measure for the relative selectivity of each ligand can be made. Aminoglycosides have a substantial affinity to poly A-poly U duplex RNA (compare column b to c, Table 4). Experiments with competing nucleic acids contain 15 ug/mL plasmid DNA (pGEM) or 15 ug/mL of polyA-polyU duplex RNA (~50-fold molar excess of DNA or RNA nucleotides, relative to the RRE. Dividing the $IC_{50}$ values in column c by column b produces a ratio proportional to the RRE selectivity of each compound (Table 4, column e). Upon guanidinylation of kanamycin A, kanamycin B, tobramycin, and paromomycin, this ratio decreases, suggesting that these compounds are more selective for the RRE than their amino precursors. Similar difference sin RRE selectivity were seen when a complex mixture of mature and pre-tRNAs (at 64 ug/mL) is used instead of poly A-poly U. This suggests that the changes in RRE selectivity, observed upon guanidinylation, is a general characteristic. For neomycin, this ratio increases upon guanidinylation, indicating a lower RRE selectivity. The lower RRE selectivity of guanidinylated neomycin is likely to reflect a general trend exhibited by highly cationic compounds; as the total charge increases, the specificity for the particular RNA typically decreases. These results demonstrate that guanidinylation impacts the RNA specificity of glycoside-based ligands. Both the aminoglycosides and the guanidinoglycosides show very little affinity for double-stranded DNA (compare column b to d, Table 4). This suggests that the core structure of the glycosides, and not the identity of the basic groups, is responsible for the RNA over DNA selectivity exhibited by both families of glycosides. The results indicate that both families of glycosides have a higher affinity to simple duplex RNA (polyA-polyU) than to simple duplex DNA. This suggests that the difference between A-form and B-form helical structure is an important determinant for glycoside recognition. The transformation of aminoglycosides into guanidinoglycosides has created a new family of compounds for the study of RNA-small molecule interactions. Our results indicate that guanidinoglycosides bind RNA preferentially over DNA, and show selectivity between various RNAs. The higher affinity and selectivity of guanidinoglycosides to the RRE implicate their potential use as antiviral agents.

The specific examples depicted above are to be understood as exemplary and do not indicate limitations of the invention, which is to be understood as limited only by the scope of the following claims.

What is claimed is:

1. A method for producing a guanidinoglycoside, said method comprising reacting a compound having the general formula:

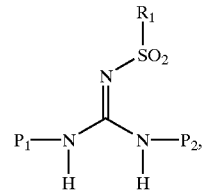

wherein $P_1$ and $P_2$ are urethane protecting groups and $R_1$ is trifluoromethane, with an aminoglycoside under conditions such that the aminoglycoside is guanidinylated, thereby producing the guanidinoglycoside.

2. The method of claim 1, wherein the aminoglycoside is tobramycin and the guanidinoglycoside is guanidinylated tobramycin.

3. The method of claim 1, wherein the aminoglycoside is glucosamine and the guanidinoglycoside is guanidinylated glucosamine.

4. The method of claim 1, wherein the aminoglycoside is kanamycin and the guanidinoglycoside is guanidinylated kanamycin.

5. The method of claim 1, wherein the aminoglycoside is neomycin and the guanidinoglycoside is guanidinylated neomycin.

6. The method of claim 1, wherein the aminoglycoside is 2-deoxystreptamine and the guanidinoglycoside is guanidinylated 2-deoxystreptamine.

7. The method of claim 1, wherein the aminoglycoside is paromomycin and the guanidinoglycoside is guanidinylated paromomycin.

8. The method of claim 1, wherein the reaction is carried out in MeOH for about 2 days with equimolar $NEt_3$.

9. The method of claim 1, wherein the reaction is carried out in a 4:1 mixture of 1,4-dioxane/$H_2O$ for about 3 days to 7 days with equimolar $NEt_3$.

10. The method of claim 1, wherein $P_1$ and $P_2$ is Boc.

11. The method of claim 10 wherein the aminoglycoside is tobramycin.

12. The method of claim 1 wherein the aminoglycoside is tobramycin.

13. The method of claim 1 wherein the aminoglycoside is glucosamine.

14. The method of claim 1 wherein the aminoglycoside is 2-deoxystreptamine.

15. The method of claim 1 wherein the aminoglycoside is kanamycin.

16. The method of claim 1 wherein the aminoglycoside is neomycin.

17. The method of claim 1 wherein the aminoglycoside is glycoside.

18. The method of claim 1 wherein the aminoglycoside is paromomycin.

19. A method for identifying a compound that binds to a HIV-1 Rev protein RNA recognition element (RRE), comprising:

incubating components comprising a test compound, the RRE, and a labeled Rev protein under conditions sufficient to allow the components to interact; and detecting the labeled Rev protein, wherein the location or emission of the labeled Rev is indicative of a test compound that binds to the RRE.

20. The method of claim 19, wherein the RRE is immobilized on a solid support.

21. The method of claim 19, wherein the Rev is labeled with fluorescent molecule.

22. The method of claim 19, wherein the components are fractionated following incubation but prior to detection.

23. The method of claim 19, wherein labeled Rev is detected by anisotropy at its emission wavelength.

24. The method of claim 19, wherein the test compound is selected from the group consisting of a protein, a peptide, a peptidomimetic, a small molecule, and a drug.

25. The method of claim 19, wherein the test compound is a guanidinoglycoside.

26. The method of claim 25, wherein the guanidinoglycoside is selected from the group consisting of guanidinylated tobramycin, guanidinylated glucosamine, guanidinylated 2-deoxystreptamine, guanidinylated kanamycin, guanidinylated paromomycin, and guanidinylated neomycin.

27. A method of treating a subject having or at risk of having a bacterial or viral infection, comprising, contacting the subject with a guanidinoglycoside in an amount sufficient to inhibit or prevent the bacterial or viral infection, wherein the guanidinoglycoside is selected according to the method of claim 19 as binding to the RRE.

28. The method of claim 27, wherein the subject is a mammal.

29. The method of claim 28, wherein the mammal is a human.

30. The method of claim 27, wherein the contacting is ex vivo.

31. The method of claim 27, wherein the contacting is in vivo.

32. The method of claim 27, wherein the contacting is by intravenous, intraperitoneal, intramuscular, subcutaneous, intracavity, or transdermal administration.

33. The method of claim 27, wherein the contacting is by oral or topical administration.

34. The method of claim 27, wherein the guanidinoglycoside is selected from the group consisting of guanidinylated tobramycin, guanidinylated glucosamine, guanidinylated 2-deoxystreptamine, guanidinylated kanamycin, guanidinylated paromomycin and guanidinylated neomycin.

* * * * *